United States Patent [19]
Persson et al.

[11] Patent Number: 5,961,787
[45] Date of Patent: Oct. 5, 1999

[54] SOLVENT EXTRACTION APPARATUS

[75] Inventors: Goran Persson, Jonstorp; Finn Alstin, Hoganas, both of Sweden

[73] Assignee: Foss Tecator AB, Hoganas, Sweden

[21] Appl. No.: 08/973,889

[22] PCT Filed: Jun. 13, 1996

[86] PCT No.: PCT/SE96/00770

§ 371 Date: Dec. 16, 1997

§ 102(e) Date: Dec. 16, 1997

[87] PCT Pub. No.: WO97/00109

PCT Pub. Date: Jan. 3, 1997

[30] Foreign Application Priority Data

Jun. 16, 1995 [SE] Sweden .................................. 9502195

[51] Int. Cl.⁶ .................................................. B01D 11/02
[52] U.S. Cl. ...................... 202/168; 202/169; 202/170; 202/189; 202/202; 202/203; 202/267.1; 203/43; 203/100; 422/260
[58] Field of Search ....................... 202/168, 169, 202/170, 268, 202, 269, 164, 270, 189, 205, 203, 267.1, 242; 422/255, 260; 196/14.54; 203/59, 43, 100

[56] References Cited

U.S. PATENT DOCUMENTS

| | | |
|---|---|---|
| 525,662 | 9/1894 | Meikle, Jr. ............................... 202/169 |
| 1,005,733 | 10/1911 | Mills ......................................... 202/169 |
| 3,441,481 | 4/1969 | Tobey ....................................... 202/169 |
| 4,006,062 | 2/1977 | Bhuchar et al. ......................... 202/170 |
| 4,255,386 | 3/1981 | Schachter et al. ...................... 422/101 |
| 4,567,020 | 1/1986 | Cognet et al. ........................... 422/259 |
| 4,869,437 | 9/1989 | Berz et al. ................................ 242/83 |
| 5,156,812 | 10/1992 | Killough ................................. 202/168 |
| 5,549,794 | 8/1996 | Mar ...................................... 202/185.1 |
| 5,677,193 | 10/1997 | Turner et al. ............................ 422/193 |
| 5,776,317 | 7/1998 | Spring et al. ........................... 202/168 |

FOREIGN PATENT DOCUMENTS

| | | |
|---|---|---|
| 2570956 | 4/1986 | Germany . |
| 741906 | 6/1980 | U.S.S.R. . |
| 1380001 | 1/1975 | United Kingdom . |
| WO 94/16791 | 8/1994 | WIPO . |

*Primary Examiner*—Virginia Manoharan
*Attorney, Agent, or Firm*—Skully, Scott, Murphy & Presser

[57] ABSTRACT

A solvent extraction apparatus which includes a heating plate, a vessel for containing a solvent, an extraction thimble to obtain a sample to be extracted from said vessel and a cooler for condensing evaporated solvent vapors. The cooler is connected to the vessel for containing the solvent, preferably by an adaptor. A lifting rod is provided which passes through the cooler which, at its lower portion, is provided with a drip rim on which the extraction thimble is detachably fixed. The thimble can be moved vertically by the lifting rod and the flow of solvent into and out of the cooler can be regulated by the lifting rod.

14 Claims, 4 Drawing Sheets

SOLVENT EXTRACTION APPARATUS

BACKGROUND OF THE DISCLOSURE

The present invention relates to a solvent extraction apparatus comprising a heating plate or the like, a boiling vessel for a solvent, an extraction thimble for a sample to be extracted and a cooler for condensing evaporated solvent vapours, which cooler preferably via an adaptor is connected to the boiling vessel, a lifting rod passing through the cooler, the rod preferably having a round cross section and in its lower part being provided with a drip rim or the like, which preferably is provided with holes and on which the thimble is detachably fixed. The drip rim or the like is intended for guiding condensed solvent to the thimble. The thimble can be moved vertically into different positions during the extraction by means of the lifting rod.

Extraction devices for analysis of fat or the like have existed for at least 100 years Modern methods known for about 30 years relates to an, extraction while boiling the sample in a solvent followed by a vapour extraction and a vapour condensate extraction at a continued boiling of the solvent. These known devices supply a great need They have however, a disadvantage since they are not wholly satisfactory from the view point of working environment Thus, solvent leaks via coolers and areas of sealing for instance. It is also necessary to move the sample between different steps which also means that solvent will get out into the premises. Therefore, there is a great need for an extraction apparatus which will emit a smaller amount of solvent to the premises.

SUMMARY OF THE INVENTION

According to the present invention it has been possible to satisfy this need and construct a solvent extraction apparatus comprising a heating plate or the like, a boiling vessel for a solvent, an extraction thimble for a sample to be extracted and a cooler for condensing evaporated solvent vapours, which cooler preferably via an adaptor is connected to the boiling vessel, a lifting rod passing through the cooler the rod preferably having a round cross section and in its lower part being provided with a drip rim or the like, which preferably is provided with holes and on which the thimble is detachably fixed. The drip rim or the like is intended for guiding condensed solvent to the thimble which thimble can be moved vertically into different positions during the extraction by means of the lifting rod. The upper part of the cooler is possibly sealed by means of a lid or the like which embraces the lifting rod and the upper part of the cooler whereby only very small amounts of solvent can get out to the environment. The cooler is furnished with a funnel shaped means preferably a concave bottom with through going, preferably peripherical holes for departing solvent vapours and with a central downwards directed outlet for condensed solvent vapours. The outlet is provided with a branch conduit which preferably debouches outside the side wall of the cooler. This outlet has the same inner diameter as the diameter of the lifting rod at a matching lower section of the lifting rod. The lifting rod is at this section shaped in such a manner by partial bevelling or the like that condensed solvent at a first boiling step and a subsequent vapour condensate extraction step can flow between the bevelled part and the adjacent inner wall of the outlet end then via the drip rim or the like to the thimble, while the passage to the branch conduit at these steps is closed by means of the remaining non-bevelled part of this section of the lifting rod which constitutes a tightening surface against the branch conduit. The lifting rod has below this partially bevelled part, a section with a smaller diameter than the main part of the lifting rod or it is bevelled at least towards the side where the branch conduct is placed. The lifting rod is below this thinner part provided with a sealing part intended at a full elevation of the lifting rod to seal against the lower part of the outlet and form a kind of bottom-valve at a third recovery step and at an optional fourth drying step when condensed solvent can pass from the upper side of the bottom between the thinner part of the lifting rod and the inner wall of the outlet via the branch conduct to a collecting vessel or the like.

An evacuation cooler is preferably connected to tile collecting vessel, whereby possible gaseous state solvent residues transferred via the branch conduit to the collecting vessel is refluxed back into this vessel. If necessary the collecting vessel can be cooled. Then of course it will be easier to keep the solvent in a condensed state.

Since the extraction apparatus according to the invention usually emits such a small amount of solvent to the environment the losses of solvent will of course be low. This makes it possible to re-use the solvent for further extractions on condition that the solvent will not be destroyed or deteriorated by oxidation or contamination during at the extraction.

The cooler can be provided with a connection for air injection supply into the extraction room. This can for instance be arranged by providing the adaptor with a device for air injection supply into the cooler. In this way the removal of solvent residues at the recovery step will of course be facilitited.

Suitably the extraction apparatus according to the invention is built into a casing which also contains a lift device and a heating device. Several extraction units usually two to six are normally placed side by side in such a casing whereby of course several extractions can be made at the same time. The casing can be connected to an external ventilation.

The appartus comprises means for a manual or automatic vertical movement of the lifting rod and/or the cooler. If manual means are used they normally consist of levers.

Preferably the lifting rod and the main part of the adaptor are made of an inert material such as polytetrafluor ethene or glass.

Many different substances can be extracted by means of the apparatus, for instance fats, oils, hydrocarbons, resins, additives and impurities. The extraction solvents can for instance be acetone, carbon tetrachloride, chloroform, diethyl ether, dichloro ethane, heptane, hexane, methanol, petroleum ether, toluene, trichlorethylene and water.

BRIEF DESCRIPTION OF THE DRAWINGS

The invention will be explained further in connection with the enclosed figures which in a somewhat schematic way shows the same embodiment of the extraction apparatus Then

DETAILED DESCRIPTION

Figure 1:
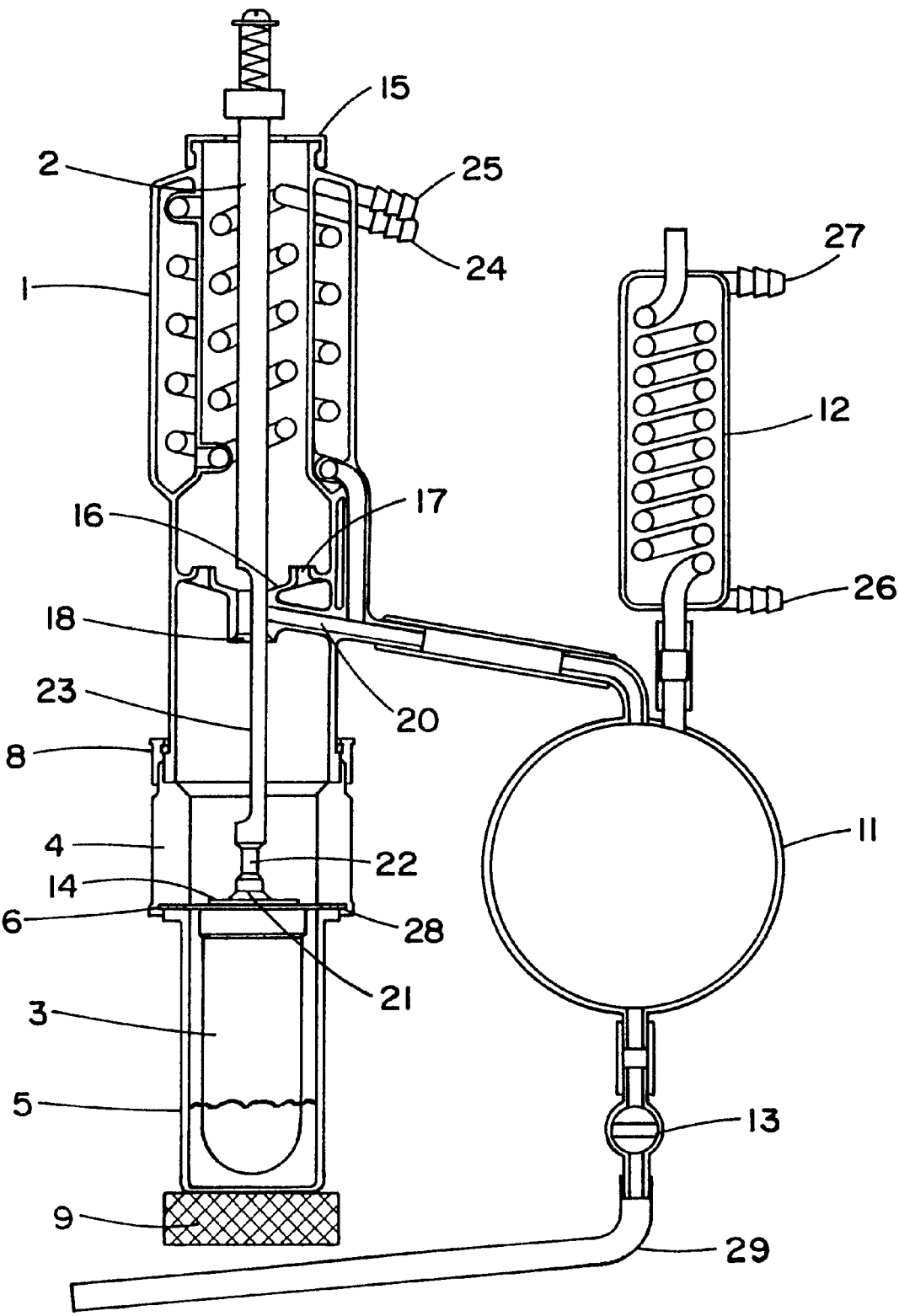
FIG. 1 illustrates the first step in the process, a so-called boiling step, FIG. 2 a subsequent vapour condensate extraction step, FIG. 3 a recovery step and FIG. 4 a drying step.

The apparatus comprises a heating plate or the like 9 a boiling vessel 5 for solvent, an extraction thimble 3 for a sample to be extracted and a cooler 1 for condensing evaporated solvent vapours. The cooler 1 is via an adaptor 4 connected to the boiling vessel 5. A lifting rod 2 passes through the cooler 1. The rod 2 has a round cross section and it is in its lower part provided with a drip rim 14 with through holes. The thimble 3 is detachably fixed to the drop rim 14. The holes are intended for passage of condensed solvent. The thimble 3 can be moved vertically by means of the lifting rod 2.

The adaptor 4 can be attached to the lower part of the cooler 1 for example by means of a mechanical joint such as a cooler nut coupling 8. According to another alternative a clamping ring arranged on the upper part of the adaptor 4 can be clamped over an outwards directed bead on the cooler 1.

The upper part of the boiling vessel 5 tightens against the lower part of the adaptor 4.

Thus, the cooler 1, the adaptor 4 and the boiling vessel 5 are firmly fixed together, but can of course easily be separated.

In certain cases it might be possible to exclude the adaptor 4. Then of course the upper part of the boiling vessel 5 must be designed in such a way that a tight connection is obtained against the lower part of the cooler 1 and that the boiling vessel easily can be separated from the cooler again.

Usually the drip rim 14 is provided with a magnet and the thimble 3 with an upper ring of magnetic metal. Then the thimble 3 can easily be attached and removed from the drip rim 14.

Figure 2:
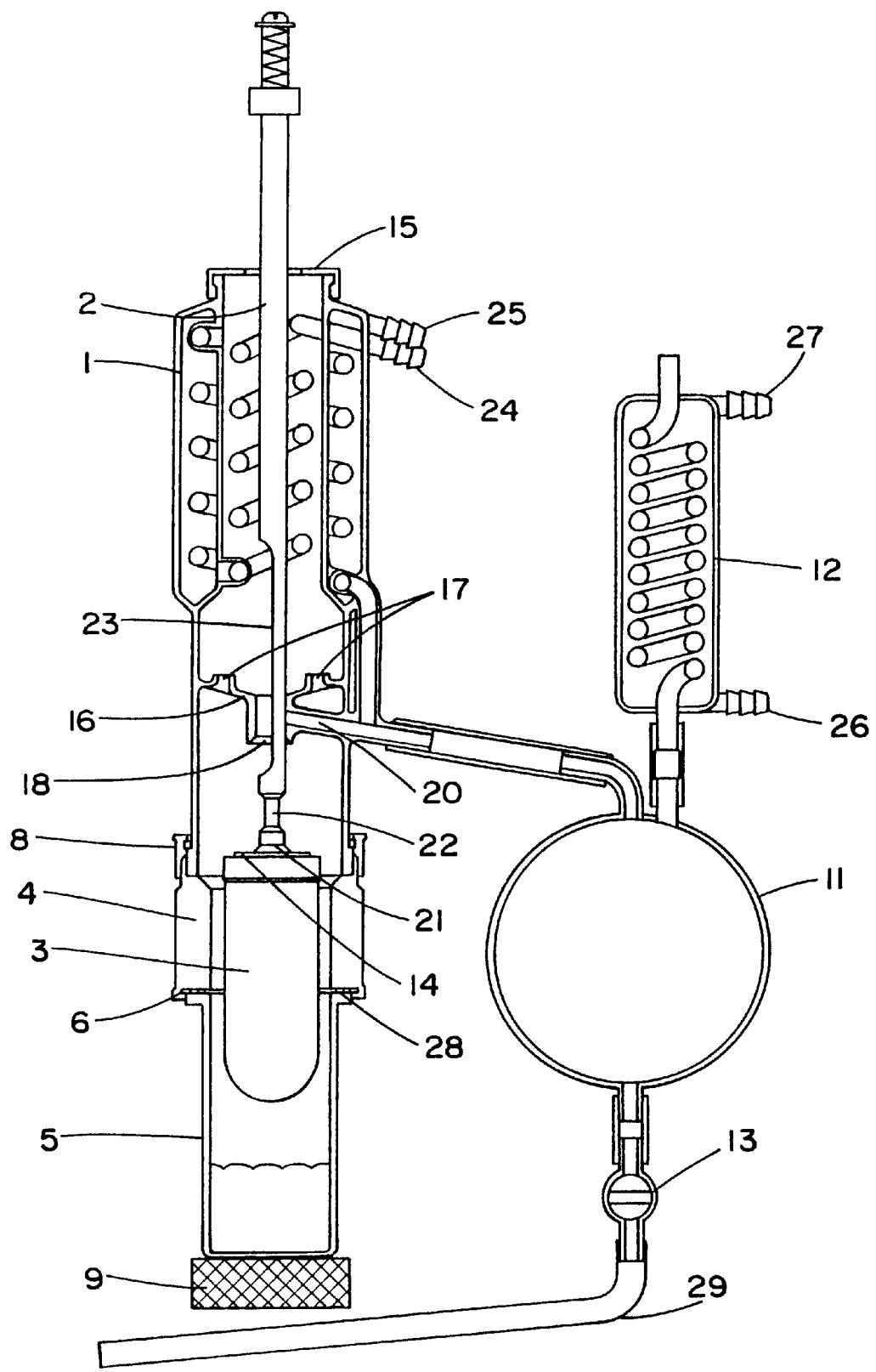

Cooling water is supplied to the cooler 1 via a nipple 25. The upper part of the cooler 1 is sealed by means of a lid or the like 15 which embraces the lifting rod 2 and the upper part of the cooler 1. In this way only very small quantities of solvent can get out into the premises. The cooler 1 is provided with a concave bottom 16 with through going peripherical holes 17 for departing solvent vapours and with a central downwards directed outlet 18 for condensed solvent vapours. The outlet 18 has a branch conduit 20. The outlet 18 has the same inner diameter as the diameter of the lifting rod 2 at a matching lower section of the lifting rod 2 On this section the lifting rod 2 has a partially bevelled part 23. Thereby at a first boiling step (FIG. 1) and a subsequent vapour condensate extraction step (FIG. 2) condensed solvent can flow between the bevelled part 23 and the adjacent inner wall of the outlet 18 and then through the holes in the drip rim 14 to the thimble 3.

Figure 3:
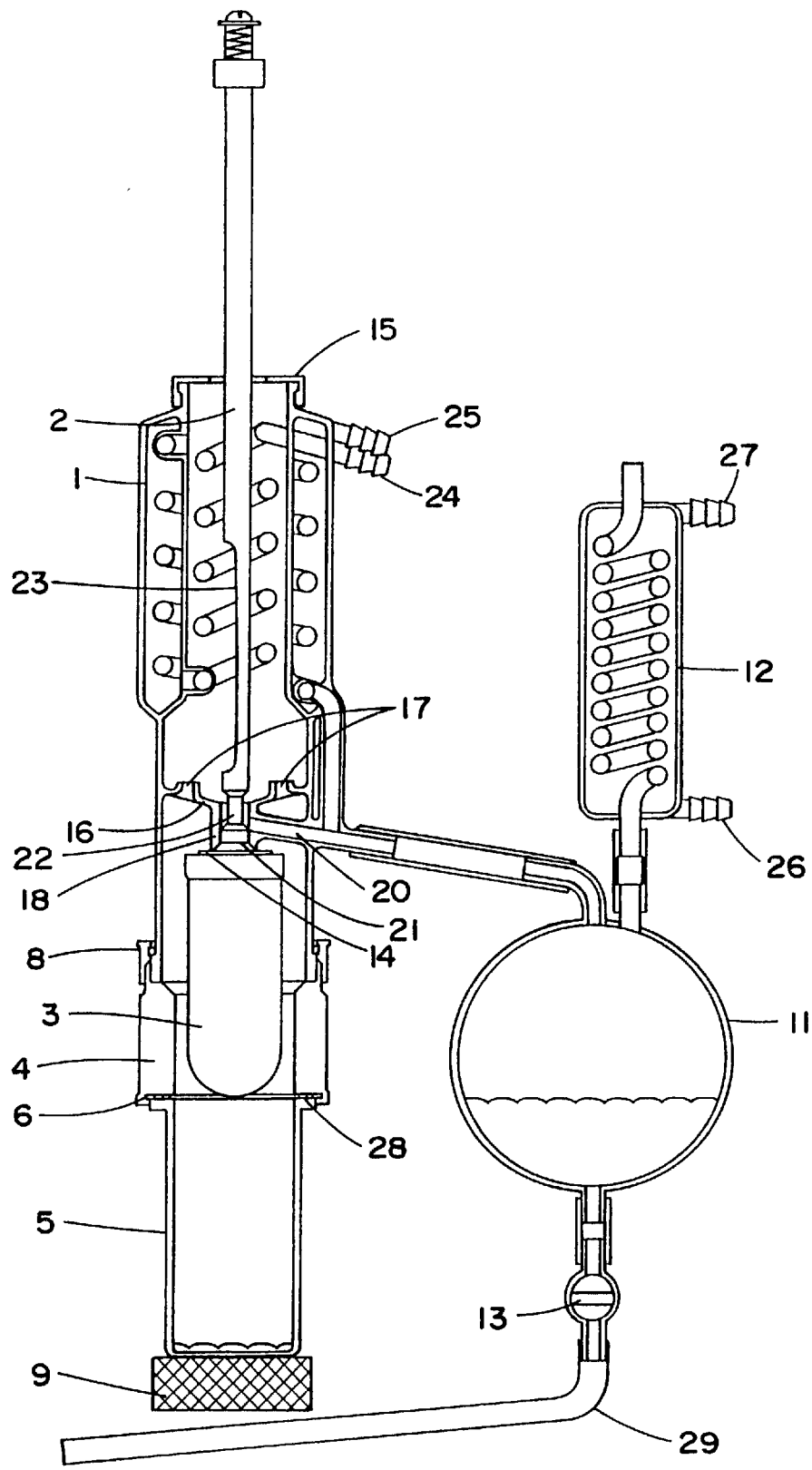
Figure 4:
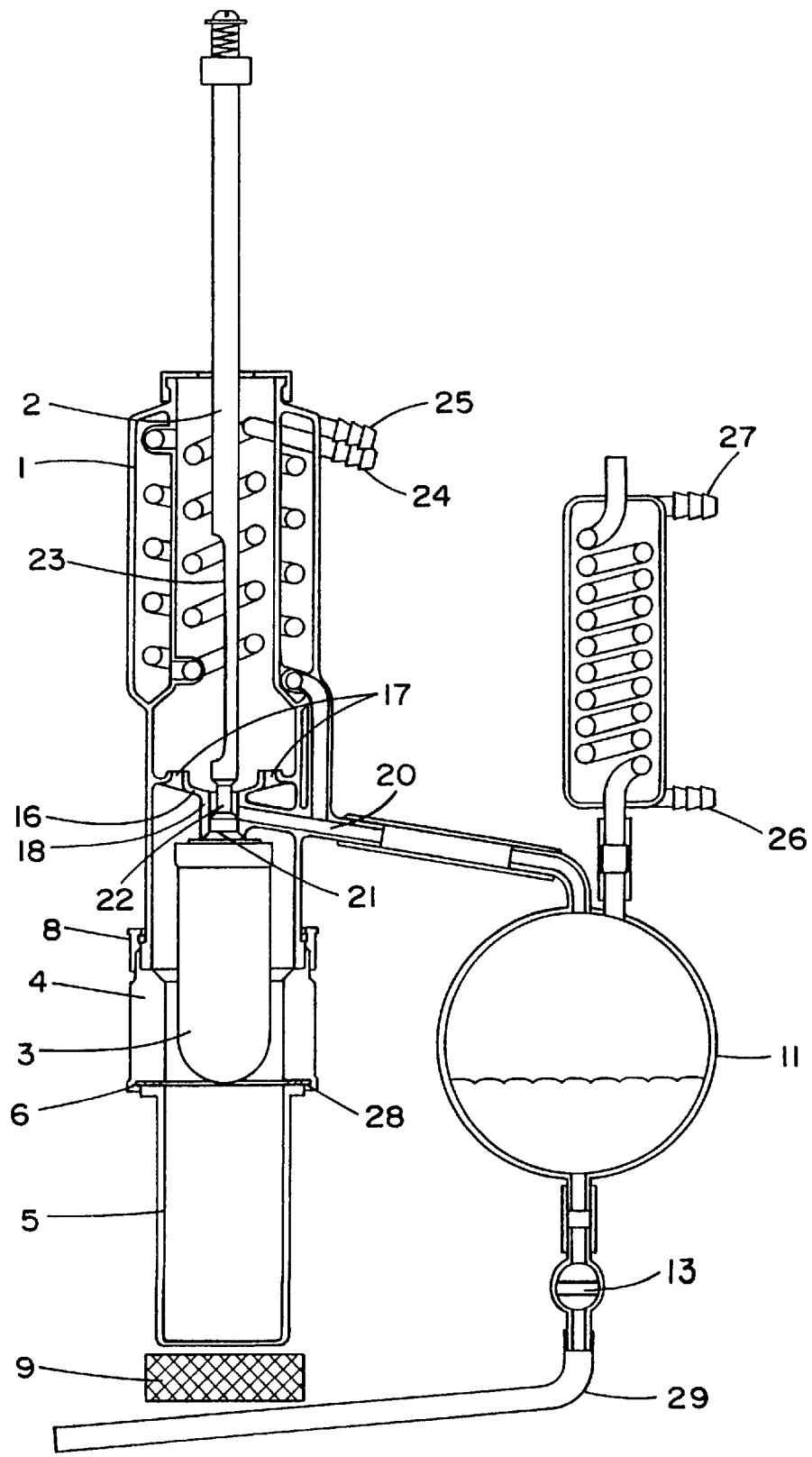

At these steps the passage to the branch conduit 20 is closed by means of the remaining non-bevelled part of this section of the lifting rod 2 which makes a tightening surface against the passage to the branch conduit 20. Below this partially bevelled part 23 the lifting rod has a section 22 with a smaller diameter than the main part of the lifting rod 2. The lifting rod 2 is below the section 22 provided with a sealing part 21 intended at full elevation of the lifting rod 2 to seal against the lower part of the outlet 18 and form a kind of bottom-valve at a third recovery step (FIG. 3) and at an optional fourth drying step (FIG. 4) when condensed solvent can pass from the upper side of the bottom 16 between the section 22 of the lifting rod 2 and the inner wall of the outlet 18 via the branch conduit 20 to a collecting vessel 11.

Of course it is necessary that the section 22 has such a length that an open connection is obtained between the upper side of the bottom 16 and the brand conduit 20 when the lifting rod is in its uppermost position.

The branch conduit 20 is connected to a collecting vessel 11 for solvent. An evacuation cooler 12 is connected to the collecting vessel Cooling water is supplied to the cooler 12 via a nipple 26 and out via a nipple 27.

The collecting vessel 11 has a drain tube 29 which has a valve 13

At the use of the extraction apparatus the adaptor 4 is fixed to the lower part of the cooler by a cooling nut coupling 8.

The sample to be extracted is weighed in the thimble 3 whereupon the upper edge of the thimble is attached to the lower side of the drip rim 14. The lifting rod 2 as well as the cooler 1 are situated in an upper position.

A solvent is filled into the boiling vessel 5 to a suitable level. Then the boiling vessel 5 is attached to the lower part of the adaptor 4 by means of a guide ring 6 which has a seal 28. The cooler 1 is lowered. So the boiling vessel 5 will rest on the heating plate 9. Then the lifting rod with the thimble 3 is lowered until the lower part of the thimble 3 with the sample will be immersed into the solvent. The heating plate 9 is heated so that the solvent boils and thereby extracts the sample in the thimble 3. The solvent then departs in the space between the sides of the thimble 3 and the boiling vessel 5 Accordingly the thimble 3 is thinner than the boiling vessel 5. The vapour state solvent passes upwards through the holes 17 in the concave bottom 16 of the cooler and is condensed in the upper part of the cooler.

The condensed solvent flows downwards and passes between the bevelled part 23 of the lifting rod 2 and the adjacent wall of the outlet 18. The branch conduit 20 is closed by means of the back part of the lifting rod 2. p The solvent flows along the lifting rod 2 down to the drip rim 14 and through the holes therein to the sample in the thimble 3.

In the next step, the vapour condensate extraction step, the lifting rod 2 is lifted up so that the thimble 3 is positioned above the surface of the solvent in the boiling vessel 5. The boiling is continued in the same way as in step 1. The passage to the branch conduit 20 is still closed. The condensed solvent passes in the same way through the outlet 18 to the thimble 3 through the holes in the drip rim 14. Since the thimble 3 is situated above the surface of the solvent in the boiling vessel 5 the sample will be leached by the condensed solvent when the solvent flows back through the thimble 3 to the boiling vessel 5.

In the third step, the recovery step the lifting rod 2 is lifted up to its uppermost position Then the outlet 18 is closed by the sealing part 21. Therefore at boiling the solvent cannot flow back to the boiling vessel 5 Instead it flows over to the collecting vessel 11 via the branch conduit 20 which is not closed any longer by the lifting rod 2. Thus, the solvent passes between the thinner section 22 on the lifting rod 2 and the wall of the outlet 18 to the branch conduit 20.

The adaptor 4 is provided with a device for air supply The device is not shown At the end of the recovery step air is supplied to remove solvent which otherwise would condense on the wall of the cooler 1 below the bottom 16.

In the last step, the drying step, the cooler 1 is lifted up so that the bottom of the boiling vessel 5 will be placed somewhat above the heating plate 9. The boiling vessel is heated carefully so that the sample will not be destroyed while the rest of the solvent is evaporated. The lifting rod 2 is in this step placed in its upper position as in the previous recovery step.

In certain cases air is supplied through the valve in the adaptor 4 at this step instead of at the recovery step. Alternatively air can be supplied in both steps. Finally the boiling vessel 5 is detached whereupon the extracted substance is taken care of for a quantitative or qualitative analysis.

The solvent in the collecting vessel 11 is removed via the conduit 29 for a possible re-use.

The invention is not limited to the embodiments shown since these can be modified in different ways within the scope of the invention. Thus, the cooler 1 can be formed in different ways. The outer cooling coil can for instance be omitted. The important thing is that the cooler is designed in such a manner that the lifting rod 2 can be used for moving the level of the thimble vertically as well as for regulating the flow of solvent in the cooler 1 and out of it.

We claim:

1. A solvent extraction apparatus comprising:

a heating means;

a boiling vessel for containing a solvent, said vessel in heating communication with said heating means, wherein said solvent is vaporized;

a cooler in communication with said vessel for condensing vaporized solvent, said cooler provided with a lid at its upper end and with a funnel shaped means at its bottom end, said funnel shaped means provided with a central downwards directed outlet for conveyance of condensed solvent vapor and with peripheral holes for conveyance of solvent vapor;

a branch conduit in communication with said central downwards directed outlet;

a collecting vessel in communication with said branch conduit;

an extraction thimble, detachably fixed to a drip rim, movable in the vertical direction by said drip rim wherein said thimble is guided to condensed solvent;

a lifting rod passing through said cooler having the same internal diameter as said central downwards directed outlet at a matching lower section of said lifting rod, said lifting rod provided with said drip rim at its lower end, said lower section of said lifting rod being bevelled such that condensate can flow between said beveled portion and an adjacent inner wall of said central downwards directed outlet, said lifting rod further provided with a smaller diameter section below said bevelled portion; and a sealing member, at the bottom end of said bevelled portion, which seals against the lower part of said central downwards directed outlet.

2. An apparatus in accordance with claim 1 including an adaptor for connecting said cooler to said vessel.

3. An apparatus in accordance with claim 2 wherein said adaptor is provided with an air supply for removal of solvent residue.

4. An apparatus in accordance with claim 2 wherein said adaptor is constructed of an inert material.

5. An apparatus in accordance with claim 4 wherein said inert material is selected from the group consisting of polytetrafluoroethylene and glass.

6. An apparatus in accordance with claim 1 wherein said heating means is a heating plate.

7. An apparatus in accordance with claim 1 wherein said lifting rod has a round cross-section.

8. An apparatus in accordance with claim 1 wherein said funnel shaped means is concave shaped and is provided with peripheral openings.

9. An apparatus in accordance with claim 1 including an evacuation cooler, connected to said collecting vessel, whereby any gaseous solvent collected in said collecting vessel is condensed.

10. An apparatus in accordance with claim 1 comprising cooling means provided about said collecting vessel.

11. An apparatus in accordance with claim 1 including means for providing vertical movement for said lifting rod.

12. An apparatus in accordance with claim 1 including means for the vertical movement of said cooler.

13. An apparatus in accordance with claim 1 wherein said lifting rod is constructed of an inert material.

14. An apparatus in accordance with claim 12 wherein said inert material is selected from the group consisting of polytetrafluoroethylene and glass.

* * * * *

UNITED STATES PATENT AND TRADEMARK OFFICE
CERTIFICATE OF CORRECTION

PATENT NO. : 5,961,787

DATED : October 5, 1999

INVENTOR(S) : Goran Persson, et al.

It is certified that error appears in the above-identified patent and that said Letters Patent is hereby corrected as shown below:

On The Title Page, [57] ABSTRACT, Line 2: "plate" should read --means--

On The Title Page, [57] ABSTRACT, Line 6: "by an" should read --by means of the--

On The Title Page, [57] ABSTRACT, Line 9: "by the" should read --by means of the--

On The Title Page, [57] ABSTRACT, Line 11: "by the" should read --by the means of--

Column 1, Line 18: "years Modern" should read --years. Modern--

Column 1, Line 22: "need they" should read --need. They--

Column 1, Line 25: "environment Thus" should read --environment. Thus--

Column 2, Line 13: "tile" should read --the--

Column 3, Line 39: "2 On" should read --2. On--

Column 3, Line 66: "vessel Cooling" should read --vessel. Cooling--

Column 4, Line 2: "13" should read --13.--

Column 4, Line 13: "lowered.So" should read --lowered so--

Column 4, Line 19: "5 Accordingly" should read --5. Accordingly--

UNITED STATES PATENT AND TRADEMARK OFFICE
CERTIFICATE OF CORRECTION

PATENT NO. : 5,961,787
DATED : October 5, 1999
INVENTOR(S) : Goran Persson, et al.

It is certified that error appears in the above-identified patent and that said Letters Patent is hereby corrected as shown below:

Column 4, Line 26: "2. p The" should read --2.--

Column 4, Line 26: "The" should begin a new paragraph.

Column 4, Line 43: "5 Instead" should read --5. Instead--

Column 4, Line 26: "2. p The" should read --2.--

Column 4, Line 26: "The" should begin a new paragraph.

Column 4, Line 50: "shown At" should read --shown. At--

Column 6, Line 35, Claim 14: "Claim 12" should read --Claim 13--

Signed and Sealed this

Twenty-seventh Day of March, 2001

Attest:

NICHOLAS P. GODICI

Attesting Officer

Acting Director of the United States Patent and Trademark Office